United States Patent [19]

Blum

[11] 4,401,890
[45] * Aug. 30, 1983

[54] PHOTON EMISSION TOMOGRAPHIC APPARATUS

[76] Inventor: Alvin S. Blum, 2350 Del Mar Pl., Fort Lauderdale, Fla. 33301

[*] Notice: The portion of the term of this patent subsequent to Jan. 11, 2000 has been disclaimed.

[21] Appl. No.: 204,304

[22] Filed: Nov. 5, 1980

Related U.S. Application Data

[63] Continuation-in-part of Ser. No. 163,057, Jun. 26, 1980.

[51] Int. Cl.³ .................................................. G01T 1/20
[52] U.S. Cl. .................................................. 250/363 S
[58] Field of Search ............... 250/360, 363 S, 445 T, 250/447, 451, 521, 522; 128/653, 654; 269/324, 325, 328, 908

[56] References Cited

U.S. PATENT DOCUMENTS 4,229,656  10/1980  Iversen et al. ...................... 250/447
4,281,249   7/1981  Lapidus ............................ 250/363 S Primary Examiner—Alfred E. Smith
Assistant Examiner—Janice A. Howell

[57] ABSTRACT

Tomographic imaging system employs rotating body support for rotating body before imaging radiation detector. Rotating body support moves toward and away from detector to follow body contours and maintain minimal body/detector distance for optimal image quality.

14 Claims, 11 Drawing Figures

U.S. Patent   Aug. 30, 1983   Sheet 1 of 3   4,401,890
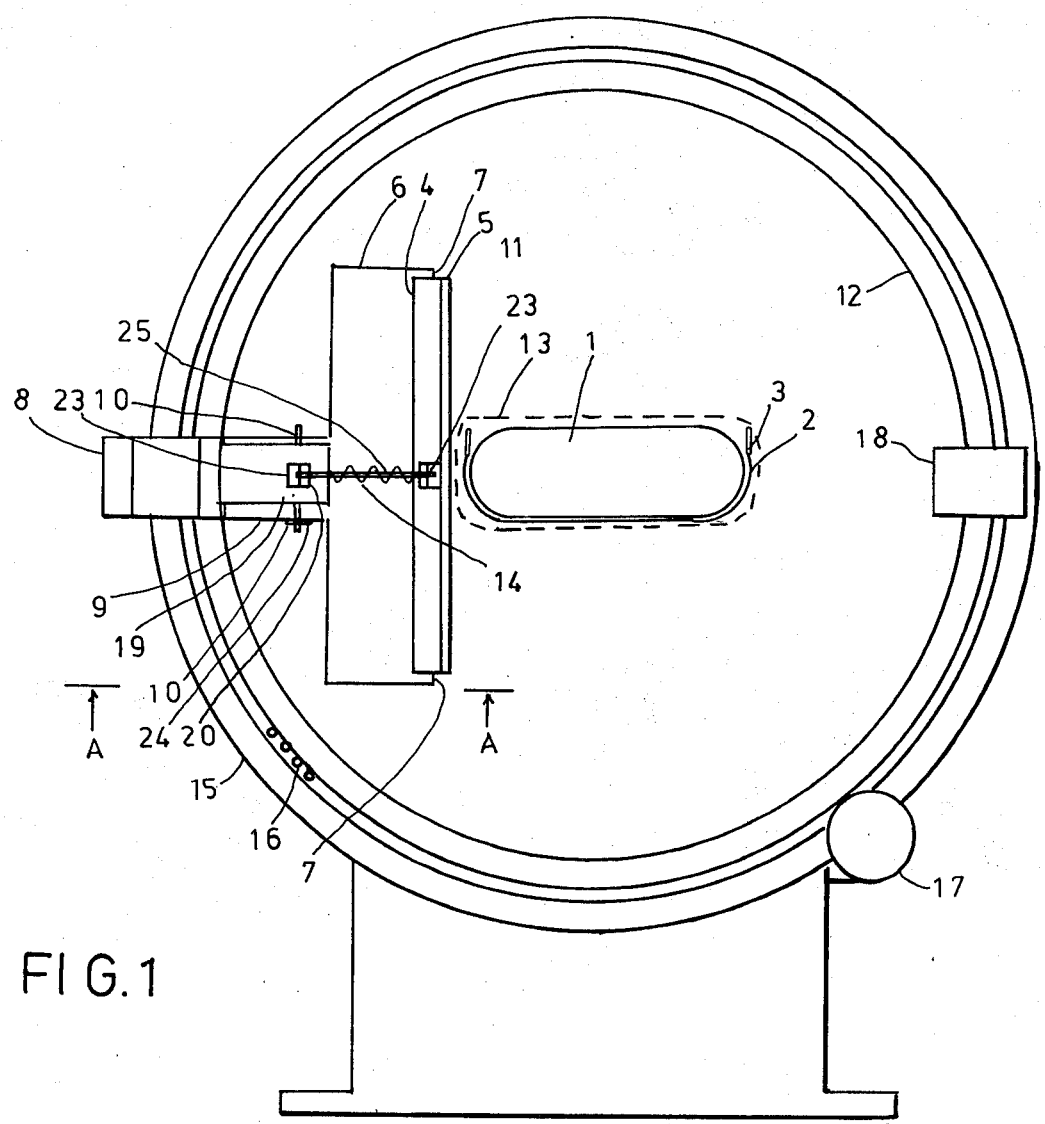
FIG.1
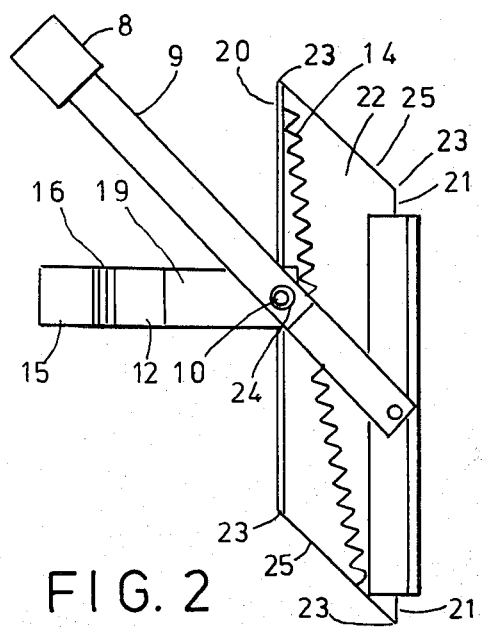
F.I.G. 2
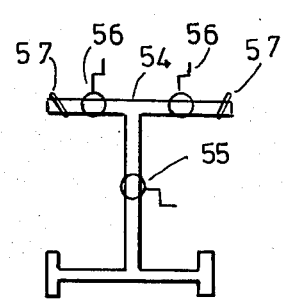
FIG.7   FIG.5
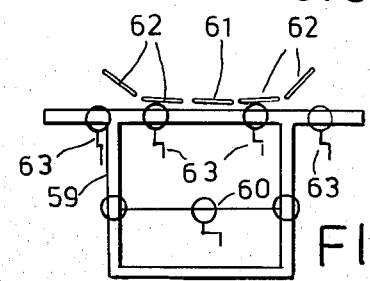
FIG.8

PHOTON EMISSION TOMOGRAPHIC APPARATUS

This is a continuation in part of copending application Ser. No. 06/163,057 filed June 26, 1980.

FIELD OF THE INVENTION

Apparatus and method for producing images of the distribution in three dimensions of photon emitting materials (radioactive pharmaceuticals) in the body including detector, detector support and body support.

DESCRIPTION OF THE PRIOR ART

Area radiation detectors of the scintillation camera type rotate around the subject containing radioactive material so as to view the radiation from a plurality of angles. Radiation detection information and detector position information are correlated by computer reconstruction to provide images of the distribution of the radioactive material within the body in a variety of views such as transverse or longitudinal slices through the body. Prior art uses one or more scintillation detectors in a rotating ring. The radius of the cylinder described by the moving face of the detector is generally fixed large enough to accommodate a large person. Resolution or image quality of these detection systems deteriorates rapidly as the subject/dectector distance increases so that a fixed radius unnecessarily sacrifices image quality in a smaller subject. General Electric Corp. has recently introduced a rotating counterbalanced detector whose radius of rotation can be adjusted before operation to a smaller cylinder to view the head or a child with shorter subject/detector distance.

However, the shape of the body and the cantilevered body support are not cylindrical, so that imaging the torso requires setting the radius to allow the detector to clear the support sides which means that when the detector is over the chest, it may be very far from the body surface, causing a loss of image resolution. Further, the geometry of the counterweight support requires a cantilevered body support. The cantilevered body support requires great strength and rigidity of construction, interfering with design for adjustability to smaller bodies and thin construction for transparency to the radiation which must pass therethrough to the detector. The counterbalance mechanism is effective mechanical engineering because the counterweight for the detector head provides rotational balance as well, so that only small uniform force for rotation is required at any angle. Unfortunately, the biological engineering is not as effective, because the rotating counterweight and ring geometry interfere with extending the arms overhead. Arms at the side increase the radius of the cylinder of rotation needlessly and also absorb imaging radiation from the torso.

SUMMARY OF THE INVENTION

It is an object of the present invention to improve image quality by minimizing subject/detector distance. The present invention allows the radius of rotation to change during rotation to conform to the body contour, maintaining minimum subject/detector distance throughout the procedure. Improved body support means allows adjustment to body size and reduces absorbing structure. Improved detector support design allows improved patient positioning, because body may now be supported and extended at both ends without interference from counterweight.

The present invention provides one or more collimated, large area radiation imaging detector devices generally of, but not limited to, the scintillation camera type, including means for supporting said detector, means for moving said detector about a radiation emitting subject so as to view the subject from a plurality of angles. Means are provided to maintain close spacing between subject and detector during said movement to achieve optimum resolution of imaging of distribution of radiation emitting material within the subject. It is a further object of the present invention to provide rotating patient support means including means for maintaining minimal distance between patient and detector during the rotation such as adjustable body contour control means. Body contour belt means may be provided to cover and approximate the body contours and to provide a sliding contact path for the detector. It is a further object of the invention to provide spring loaded detector support means to gently and yieldably press the detector against the body contours, body support means, body contour belt means and the like during its movement or rotation about the body. The body and detector act generally as cam and cam follower in this operation. Surfaces of a lubricous nature and guides on the leading edge of the detector may be provided to facilitate smooth movement therebetween. Counterweight means are provided at the opposite end of the detector support means to balance the mass of the detector so that as it moves in space, the only force of the face of the detector against the body, belt, or the like is a controlled spring force. Support counterweight means may be further provided to balance the weight of the entire detector with its support means and counterweight means, thereby allowing the movement of the detector about the subject with relatively small and uniform force by support driving means. Improved body support means are provided allowing adjustment to body size and shape. Said body support means facilitate patient handling and positioning, reduce radiation absorbtion and enable closer patient/detector spacing.

BRIEF DESCRIPTION OF THE DRAWINGS

FIG. 1 is a front view of an embodiment of the invention wherein the detector, as it adjusts to body contours, swings in a plane parallel to the axis of rotation around the body.

FIG. 2 is a partial cross section through line A—A of FIG. 1.

FIG. 5 is an end view of the flexible web body support means in use for patient transfer.

FIG. 7 is an end view of one adjustable end support, for flexible web body support means.

FIG. 8 is an end view of rigid plank body support means.

FIGS. 1 and 2 show in front view and partial section through line A—A of FIG. 1 respectively, a tomographic system of the present invention. Radiation from the patient 1, supported in fabric sling 2, suspended from rigid longitudinal members 3, is detected by scintillation camera detector 4, having parallel hole collimator 5. Detector 4 is held in yoke 6 at pivot points 7. Detector counterweight 8 balances weight of the detector in any position so that only a small force is required to swing detector support arm 9 about pivots 10 to move collimator face 11 into or out of inner ring 12 to maintain contact with flexible body contour belt 13 wrapped around the patient at the level of the detector. Tension spring 14 provides this small, controlled force, gently following the patient contours as inner ring 12 rotates inside stationary outer ring 15 on roller bearings 16, driven by small motor 17. Assembly counterweight 18 balances entire weight of detector, detector counterweight, and detector support assembly so that only a small driving force is required. A second detector and support may replace this counterweight. Use of small spring force and small drive motor reduce potential hazard to patient. Detector support arm pivots 10 are fastened to inner ring projection 19, whose center line is always on a radius of rotation of inner ring 12. Also fastened to projection 19 are parallelogram arms 20. Parallelogram bars 25 connect arm 20 to projections 21 at opposite ends of the detector by pivots 22 to form a parallelogram with a diagonal spring 14. In any position of the detector as it swings in and out while following the body contour as inner ring 12 rotates, parallelogram action will maintain the collimator face 11 in a plane parallel to the axis of rotation of ring 12. This geometry facilitates tomographic reconstruction. Drive motor 17 may rotate the inner ring in uniform increments, e.g. 36 steps of 10° each; pausing at each step to accummulate radiation data from angles all around the body. Alternatively the ring may turn and data may be input continuously. Computer processing and display means, not illustrated, accumulate and process the input radiation and position data and provide useful images of the distribution of radiation emitting material in the body. As the detector rotates to measure the patient from all angles, it is desirable that there be no longitudinal motion of the patient relative to the detector i.e. motion along the axis of rotation of ring 12. Unfortunately, as detector 4 swings in support arm 9 around pivots 10, this longitudinal motion does occur. Fortunately, the amount of longitudinal motion can be calculated if the angle of arm 9 with projection 19 is known. Rotary position indicator 24 provides this information to the computer, which calculates the longitudinal position and displaces the incoming data by this distance, thereby correcting for the motion. A small portion of the caudad and rostrad edges of the field of view will thereby have incomplete data and may not be as useful. Alternatively, the patient or detector assembly may be moved by mechanical means the corresponding distance. FIG. 3 is a front view and FIG. 4 is a partial section through B—B of FIG. 3 of another tomographic system embodying the invention. A collimated detector 29, held in yoke 30 is counterbalanced by 2 detector counterweights 31 at end of dectector support arms 32 pivoted at pivots 33 in inner ring projection 34 carried by inner ring 35 which rotates on roller bearings 36 inside stationary outer ring 37. Inner ring also carries spring supports 39. Tension springs 40 between supports 39 and arms 32 force detector face toward center of ring and against the body of the patient, not shown. As ring 35 rotates around the body, the detector gently, by action of springs 40, follows the contour of the body, body support, body contour covering belt wrapped around the body, or the like. Detector assembly counterweight 41, fastened to ring 35 balances the mass of the detector assembly so that very low force drive motor 42 can rotate ring 35 around the patient.

Figure 3:
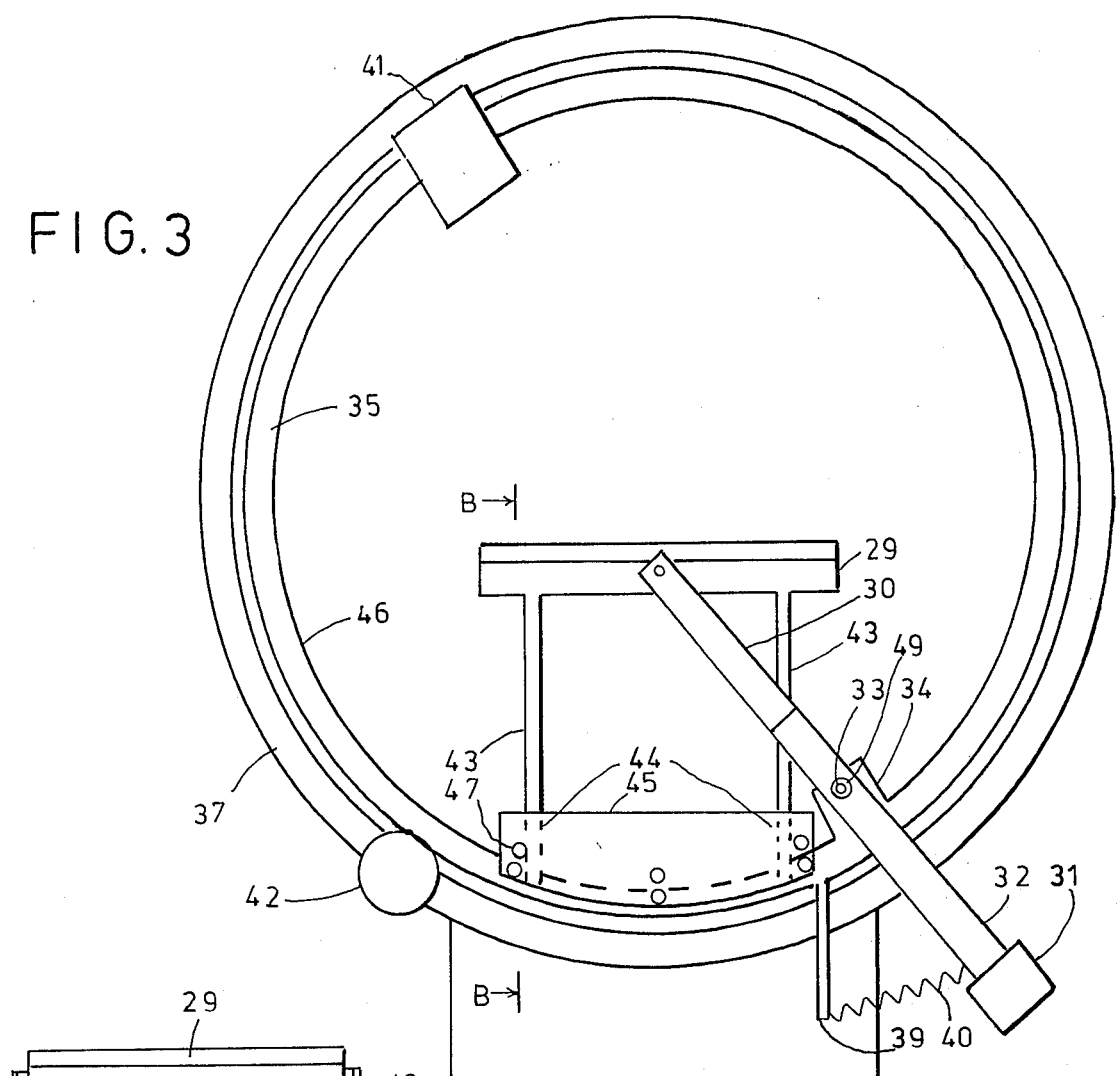
FIG. 3 is a front view of an embodiment wherein the detector as it adjusts to body contours, swings in a plane perpendicular to the axis of rotation around the body.

The detector support arm of the embodiment in FIG. 1 moves in a plane parallel to the axis of the ring, whereas the detector support arm of FIG. 3 moves in a plane perpendicular to the axis of the ring. Different correcting means to maintain geometry suitable for tomography are therefor required. In order to keep the same point on the face of detector 29 perpendicular to a radius of ring 35 as arms 32 swing through an arc, rods 43 are rigidly fastened at right angles to the back of detector 29. Rods 43 slide in sleeves 44 in light weight flange rider 45, which rides on flange 46 on inner edge of inner ring 35 on rollers 47. Uniform angular incremental rotation of ring 35 will not result in uniform angular rotation of detector 29 if the angle of arm 32 with spring support 39 changes. Rotary position indicator 49 detects the angle and feeds that information into the computer. The computer can then operate drive motor 42 to achieve the appropriate rotational angle of the detector.

Figure 6:
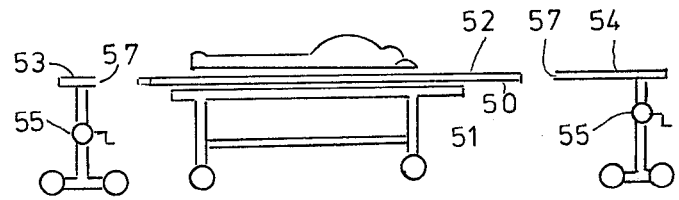
FIG. 6 is a side view of the flexible web support means.

FIGS. 5, 6, 7 illustrate a body support system for rotational tomography employing a flexible web such as a stiff dacron fabric sling or hammock 50. It is shown resting on a conventional patient transport stretcher 51 in FIGS. 5 and 6. Rigid, longitudinal, radiolucent, support members 52 may be permanently fastened to edges of sling 50, or may slide into edge pockets after patient is moved onto sling to reduce discomfort. The stretcher 51 is rolled into place with overhanging members 52 projecting into the ring. Long adjustable end support 54 is rolled into place from the opposite face of the ring and adjusted for height with adjustor 55 and for width with adjustor 56 until longitudinal members 52 fit into sockets 57. Short adjustable end support 53 is now fitted to the other ends of the members 52. Width and height of the sling are adjusted to remove the stretcher 51 and to center the region of the body for optimum tomography.

FIG. 8 illustrates a body support system which remains in place straddling the rotating ring with an end support 59 at each end, having height adjustor 60. The body is supported therebetween by rigid radiolucent planks 62 and 61. All four side planks 62 are adjustable by adjustors 63 and also removable. With all the planks in place and flat, the patient is positioned by sliding. The planks are removed or adjusted as required by body size and contour. To facilitate detector head movement and reduce patient trauma, a body contour belt may be wrapped around the body at the level to be traversed by the detector. Body contour belt may be a wide band of thin metal, heavy plastic or fabric having thick edges to raise the belt off the body slightly. The edges are far enough apart to be beyond the caudad and rostrad edges of the field of view of the detector.

Figure 9:
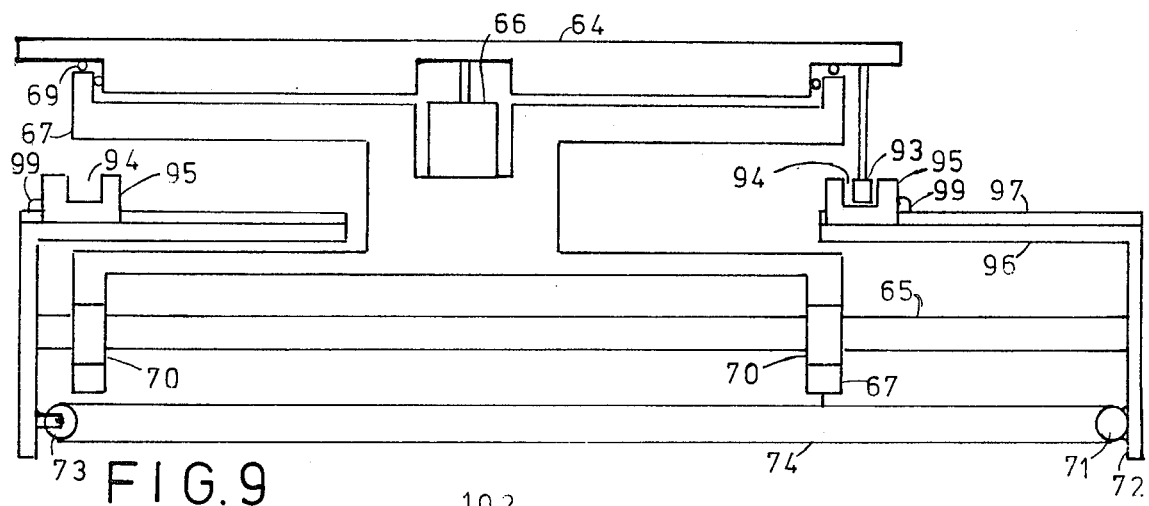
FIG. 9 is a side view of patient rotator with power translator.
Figure 11:
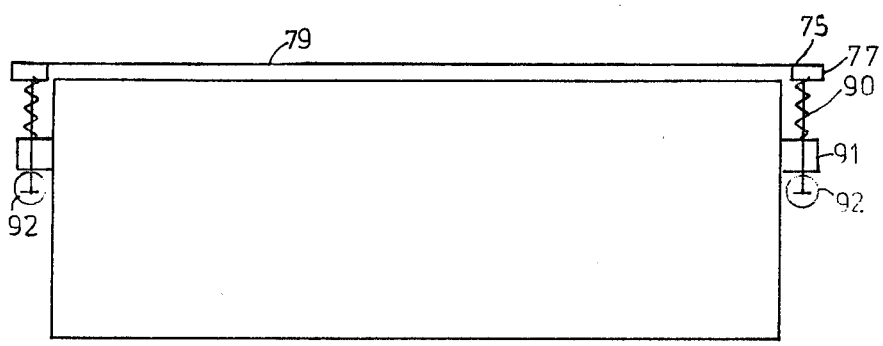
FIG. 11 is a sectional view of body contour sensor on detector.

In the embodiment of FIG. 9, the patient sits on platform 64 which rotates in front of a stationary detector. While rotating, patient and platform move to and fro on rails 65 to maintain minimal distance between patient and detector. Motor 66, which may include slip clutch and rotary position indicator, connected to platform support 67 rotates the platform born by radial thrust bearing 69. Platform support 67 rides on rails 65 on friction reducing ball bushings 70. Two means for control of to and fro motion for following body contours are shown. In the first means for control, reversible motor 71, connected to rail support 72, with pulley 73, and cable 74 connected to platform support 67 can move the platform support to and fro. Motor operates in conjunction with body contour sensor 75 shown clamped on detector 29 of FIG. 11 in which frame 77 for membrane 79 is supported by springs 90 connected to clamp 91. Any pressure or contact by patient, patient support, body contour belt or the like against any portion of membrane 79 or frame 77 actuates any of a plurality of switches 92. The imaging process includes the following steps: 1. With patient at rest in contact with membrane 79 and switch 92 actuated, detector detects until completion of imagimg interval. 2. Motor 71 moves patient away from detector until switch 92 is released. 3. Motor 66 then rotates patient 10°. Motor 71 then moves patient toward detector until switch 92 is actuated. A slip clutch means limits force with which patient is driven into the detector. 5. Next imaging interval begins. In the event switch 92 is actuated during rotation step 3, motor 66 stops and step 2 begins again. This may be repeated until 10° rotation is achieved.

Figure 4:
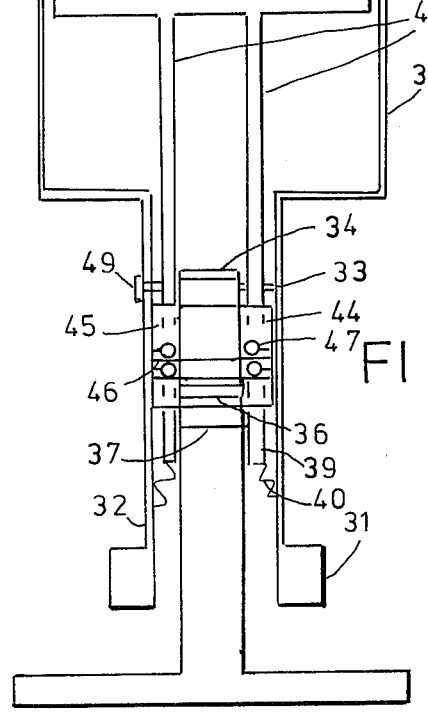
FIG. 4 is a partial cross section through line B—B of FIG. 3.

This method of achieving minimum patient/detector distance may be applied to the rotating detector embodiments by replacing spring means 40 of FIGS. 3 and 4 and spring means 14 of FIGS. 1 and 2 by reversible motor drive means. Sensing by pressure on a membrane surface may be replaced by indirect sensing means such as a grid of light beams.

Another method of control of to and fro motion employs roller 93 connected to rotating platform 64 rolling in groove 94 of one of a plurality of track sections 95 which are radially arranged on stationary annular disc 96 carrying rails 97. Each track section 95 slides radially on an individual rail 97, but all sections can be prevented from sliding by lock means 99. Imaging is preceded by a body contour adjustment process: Lock 99 is unlocked. As patient is rotated, platform support 67 is adjusted manually for desired patient/detector spacing at each rotation. This moves the track sections 95 on rails 97. Locks 99 are then locked. Now, when motor 66 rotates platform 64, roller 93 will follow grooves 94 in all track sections 95, thereby moving platform support, platform and patient to and fro to positions set in adjustment process.

Figure 10:
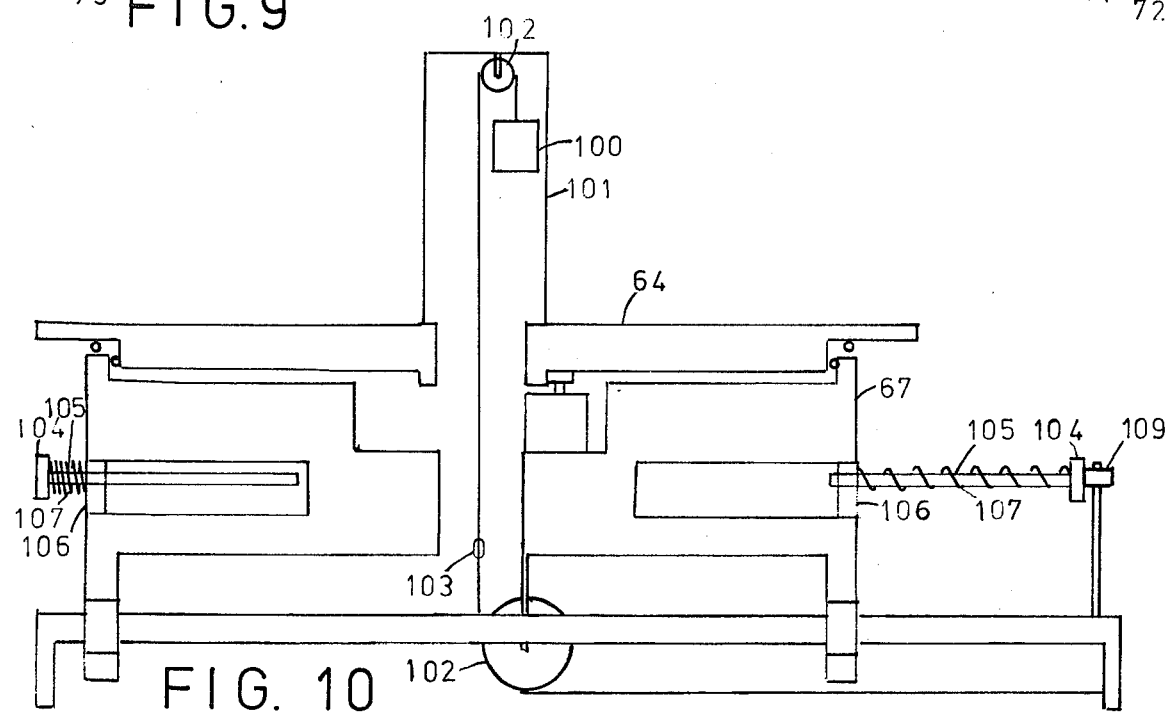
FIG. 10 is a side view of patient rotator with counterweight.

FIG. 10 shows a patient rotating platform 64 on platform support 67 whose to and fro motion is provided by counterweight 100 on cable 101 over pulleys 102 which pulls platform support toward the detector with a small controlled force. That motion is limited by contact between the detector and the patient, body contour belt means or the like. Swivel 103 in the cable prevents twisting during rotation. Alternatively, motive force may be provided by spring means. Alternatively, motion toward the detector may be limited and controlled by adjustable body contour belt means adjacent the body as illustrated by belt 104 supported by radial rods 105 which slide radially in locking and releasing ratchet slides 106, compressing springs 107. Roller 109 bears against belt 104 thereby controlling motion of platform support 67.

The belt is unlocked and adjusted manually to the body contour in an adjustment process and then locked before beginning the imaging process. Adjustable belt means may be incorporated into a head support. Head support may be pivotally suspended from a non rotating arm connected to the platform support. Adjustable patient support means atop the rotating platforms of FIGS. 9 and 10 may be an adjustable chair with back and head supports or a saddle type to limit knee flexing.

Anatomy not seen by the detector from all angles will not be optimally imaged. Location of the patient support on a rotating platform may be adjusted so that the center of rotation passes through the center of the organ being imaged.

Inasmuch as the present invention is subject to many variations, modifications and changes in detail, it is intended that all matter described above or shown in the accompanying drawings be interpreted as illustrative and not in a limiting sense.

What is claimed is:

1. A body rotational imaging system for radiation detector means, comprising: body support means; body support rotation means; and body contour following means, said body contour following means causing the surface of said body to be adjacent to a face of said detector means to maintain a minimum distance between said detector means and said body as said body is rotated before said detector means for improved image resolution.

2. The invention of claim 1, wherein said body contour following means includes translatory motion means for moving said rotational body support means toward or away from said detector means.

3. The invention of claim 1 including sensor means connected to said detector means, said sensor means sensing the proximity of said body, and said body support means for control of said minimum distance.

4. The combination of claim 3, wherein said sensor controls motion of said body support means toward or away from said detector means.

5. Invention of claim 2, wherein said translatory motion means includes a counterweight drive means.

6. The invention of claim 2, wherein said translatory motion means includes spring drive means.

7. The invention of claim 2, wherein said translatory motion means includes motor drive means.

8. The invention of claim 2, wherein said translatory motion means includes track following means.

9. The invention of claim 2, wherein said body contour following means includes adjustable contour belt means.

10. The invention of claim 2, wherein safety clutch means are provided to prevent application of excessive force of said body against said detector means.

11. Invention of claim 1 including position information storage means and position following means, said position information storage means storing detector position information generated during preliminary rotation of said body while manually adjusting said system for minimum detector/body distance, and said position following means automatically reproducing the positions of the preliminary manual operation using said stored position information during a subsequent rotation.

12. A structure for a radiation imaging system having radiation detector means for emission tomography analysis of a patient, comprising: detector support means; rotation means for rotating said detector means about an axis and around said patient so as to view said patient from a plurality of angles; radius adjusting means to adjust the radius of rotation of said detector means during said rotation to maintain a minimum distance between said detector means and said patient; and sensor means connected to said detector means, said sensor means sensing the proximity of said patient to said detector means for control of said minimum distance.

13. A rotational tomographic imaging system for detecting and displaying the distribution in depth of radiation emitting materials within a body with rotating radiation detector means and body support means including: rigid longitudinal member means for supporting said body; adjustable end member support means for adjusting and supporting said member means, said adjustable end member support means providing a first, generally flat configuration of said body support means to facilitate transfer of said body, and a second configuration, generally conforming to the contours of said body to minimize body/detector distance during detector rotation.

14. The invention of claim 13 including flexible body support web means, said rigid longitudinal member means supporting said web means.

* * * * *